(12) United States Patent
Burbank

(10) Patent No.: US 7,040,142 B2
(45) Date of Patent: May 9, 2006

(54) METHOD AND APPARATUS FOR LEAK DETECTION IN BLOOD CIRCUITS COMBINING EXTERNAL FLUID DETECTION AND AIR INFILTRATION DETECTION

(75) Inventor: Jeffrey H. Burbank, Boxford, MA (US)

(73) Assignee: Nxstage Medical, Inc., Lawrence, MA (US)

( * ) Notice: Subject to any disclaimer, the term of this patent is extended or adjusted under 35 U.S.C. 154(b) by 36 days.

(21) Appl. No.: 10/037,429

(22) Filed: Jan. 4, 2002

(65) Prior Publication Data

US 2003/0126910 A1     Jul. 10, 2003

(51) Int. Cl.
*G01M 3/04*     (2006.01)

(52) U.S. Cl. ............................................ 73/40; 340/605

(58) Field of Classification Search .............. 73/40, 73/49.2, 40.5 R, 19.1; 340/605, 612; 422/44, 422/68.1; 210/739, 321.71, 85
See application file for complete search history.

(56) References Cited

U.S. PATENT DOCUMENTS

| | | | |
|---|---|---|---|
| 3,648,694 A | | 3/1972 | Mogos et al. |
| 3,976,574 A | * | 8/1976 | White ........................ 210/188 |
| 3,985,134 A | | 10/1976 | Lissot et al. |
| 4,144,884 A | | 3/1979 | Tersteegen et al. |
| 4,148,314 A | * | 4/1979 | Yin ........................... 604/6.11 |
| 4,181,610 A | | 1/1980 | Shintani et al. |
| 4,202,332 A | | 5/1980 | Tersteegen et al. |
| 4,324,662 A | | 4/1982 | Schnell |
| 4,364,261 A | * | 12/1982 | Askwith et al. ................ 73/40 |
| 4,648,866 A | | 3/1987 | Malbrancq et al. |
| 4,788,851 A | * | 12/1988 | Brault ........................ 73/49.2 |
| 4,885,087 A | | 12/1989 | Kopf |
| 4,995,268 A | * | 2/1991 | Ash et al. ................ 73/861.05 |
| 5,011,607 A | | 4/1991 | Shinzato |
| 5,120,303 A | | 6/1992 | Hombronckx |
| 5,153,141 A | * | 10/1992 | Hobbs ........................ 436/168 |
| 5,178,763 A | | 1/1993 | Delaunay |
| 5,198,776 A | * | 3/1993 | Carr ........................... 324/639 |
| 5,248,616 A | * | 9/1993 | Beckman et al. ........... 436/116 |
| 5,252,213 A | * | 10/1993 | Ahmad et al. .............. 210/542 |
| 5,339,672 A | * | 8/1994 | Spicar ......................... 73/19.1 |
| 5,368,555 A | | 11/1994 | Sussman et al. |
| 5,394,732 A | * | 3/1995 | Johnson et al. .............. 73/19.1 |
| 5,468,390 A | | 11/1995 | Cuvello et al. |

(Continued)

FOREIGN PATENT DOCUMENTS

GB     99/24145     9/1998

OTHER PUBLICATIONS

IEC, International Standard, "Medical Electrical Equipment, Part 2-16," 1998, Second Addition.

(Continued)

*Primary Examiner*—Hezron Williams
*Assistant Examiner*—Rodney Frank
(74) *Attorney, Agent, or Firm*—Proskauer Rose LLP

(57) ABSTRACT

One of the most significant safety concerns in the automation of extracorporeal blood treatments such as dialysis is the risk of blood leakage. Extracorporeal blood treatment systems draw blood at such a high rate that a loss of integrity in the blood circuit can be catastrophic. There are a number of mechanisms for detecting and preventing leaks and/or air infiltration, but none is perfect. According to the present invention, multiple inputs are combined to provide greater security against leakage and/or air infiltration by providing sensors for external presence of liquid (plasma, replacement fluid, blood, etc.) outside a fluid circuit and infiltration of air or bubbles into the fluid circuit.

13 Claims, 4 Drawing Sheets

U.S. PATENT DOCUMENTS

| | | | |
|---|---|---|---|
| 5,515,713 A * | 5/1996 | Saugues et al. | 73/19.03 |
| 5,591,344 A * | 1/1997 | Kenley et al. | 210/636 |
| 5,605,630 A | 2/1997 | Shibata | |
| 5,624,551 A * | 4/1997 | Baumann et al. | 210/134 |
| 5,630,935 A * | 5/1997 | Treu | 210/130 |
| 5,651,893 A * | 7/1997 | Kenley et al. | 210/636 |
| 5,670,050 A * | 9/1997 | Brose et al. | 210/646 |
| 5,674,390 A * | 10/1997 | Matthews et al. | 210/261 |
| 5,674,404 A * | 10/1997 | Kenley et al. | 210/741 |
| 5,679,245 A * | 10/1997 | Manica | 210/134 |
| 5,690,821 A * | 11/1997 | Kenley et al. | 210/195.1 |
| 5,690,831 A * | 11/1997 | Kenley et al. | 210/646 |
| 5,702,606 A * | 12/1997 | Peter et al. | 210/646 |
| 5,705,066 A * | 1/1998 | Treu et al. | 210/233 |
| 5,707,086 A * | 1/1998 | Treu et al. | 285/93 |
| 5,714,060 A * | 2/1998 | Kenley et al. | 210/194 |
| 5,725,776 A * | 3/1998 | Kenley et al. | 210/646 |
| 5,762,782 A * | 6/1998 | Kenley et al. | 210/85 |
| 5,783,072 A * | 7/1998 | Kenley et al. | 210/195.2 |
| 5,817,043 A | 10/1998 | Utterberg | |
| 5,830,365 A | 11/1998 | Schneditz | |
| 5,863,421 A * | 1/1999 | Peter et al. | 210/134 |
| 5,894,011 A | 4/1999 | Prosl et al. | |
| 5,910,252 A * | 6/1999 | Truitt et al. | 210/645 |
| 6,044,591 A | 4/2000 | Kenley et al. | |
| 6,044,691 A | 4/2000 | Kenley et al. | |
| 6,090,048 A | 7/2000 | Hertz et al. | |
| 6,177,049 B1 | 1/2001 | Schnell et al. | |
| 6,187,207 B1 * | 2/2001 | Brauer | 210/739 |
| 6,189,388 B1 | 2/2001 | Cole et al. | |
| 6,221,040 B1 | 4/2001 | Kleinekofort | |
| 6,228,271 B1 * | 5/2001 | Cote | 210/739 |
| 6,269,679 B1 * | 8/2001 | McCarthy et al. | 73/19.1 |
| 6,277,329 B1 * | 8/2001 | Evans | 422/80 |
| 6,280,632 B1 * | 8/2001 | Polaschegg | 210/739 |
| 6,284,142 B1 | 9/2001 | Muller | |
| 6,327,895 B1 * | 12/2001 | Jeppsson et al. | 73/40 |
| 6,401,518 B1 * | 6/2002 | O'Keeffe et al. | 73/19.01 |
| 6,530,262 B1 * | 3/2003 | Esser | 73/40.5 R |
| 6,572,576 B1 * | 6/2003 | Brugger et al. | 604/4.01 |
| 6,585,675 B1 * | 7/2003 | O'Mahony et al. | 604/4.01 |
| 6,890,315 B1 * | 5/2005 | Levin et al. | 604/6.09 |
| 2001/0039441 A1 | 11/2001 | Ash | |
| 2002/0085952 A1 | 7/2002 | Ellingboe et al. | |
| 2002/0147423 A1 * | 10/2002 | Burbank et al. | 604/6.16 |
| 2002/0151804 A1 * | 10/2002 | O'Mahony et al. | 600/504 |
| 2003/0009123 A1 * | 1/2003 | Brugger et al. | 604/4.01 |
| 2003/0128125 A1 * | 7/2003 | Burbank et al. | 340/605 |
| 2003/0128126 A1 * | 7/2003 | Burbank et al. | 340/605 |
| 2004/0030277 A1 * | 2/2004 | O'Mahony et al. | 604/4.01 |
| 2004/0054315 A1 * | 3/2004 | Levin et al. | 604/5.01 |

OTHER PUBLICATIONS

IEC, International Standard, "Conincal Fittings With 6% (Luer) Taper For Syringes, Needles and Certain Other Medical Equipment, Part 2," 1998, Second Amendment.

* cited by examiner

METHOD AND APPARATUS FOR LEAK DETECTION IN BLOOD CIRCUITS COMBINING EXTERNAL FLUID DETECTION AND AIR INFILTRATION DETECTION

FIELD OF THE INVENTION

The present invention relates to the detection of a leak (including needle-disconnects and other causes of loss of integrity) in extracorporeal blood circuits and more particularly to the use of a combination of the detection of air and blood escaping from the blood circuit to increase responsiveness, sensitivity, and reliability of detection of leaks.

BACKGROUND

Many medical procedures involve the extraction and replacement of flowing blood from, and back into, a donor or patient. The reasons for doing this vary, but generally, they involve subjecting the blood to some process that cannot be carried out inside the body. When the blood is outside the patient it is conducted through machinery that processes the blood. The various processes include, but are not limited to, hemodialysis, hemofiltration, hemodiafiltration, blood and blood component collection, plasmaphresis, aphresis, and blood oxygenation.

One technique for extracorporeal blood processing employs a single "access," for example a single needle in the vein of the patient or a fistula. A volume of blood is cyclically drawn through the access at one time, processed, and then returned through the same access at another time. Single access systems are uncommon because they limit the rate of processing to half the capacity permitted by the access. As a result, two-access systems, in which blood is drawn from a first access, called an arterial access, and returned through a second access, called a venous access, are much faster and more common. These accesses include catheters, catheters with subcutaneous ports, fistulas, and grafts.

The processes listed above, and others, often involve the movement of large amounts of blood at a very high rate. For example, 500 ml. of blood may be drawn out and replaced every minute, which is about 5% of the patient's entire supply. If a leak occurs in such a system, the patient could be drained of enough blood in a few minutes to cause loss of consciousness with death following soon thereafter. As a result, such extracorporeal blood circuits are normally used in very safe environments, such as hospitals and treatment centers, and attended by highly trained technicians and doctors nearby. Even with close supervision, a number of deaths occur in the United States every year due to undue blood loss from leaks.

Leaks present a very real risk. Leaks can occur for various reasons, among them: extraction of a needle, disconnection of a luer, poor manufacture of components, cuts in tubing, and leaks in a catheter. However, in terms of current technology, the most reliable solution to this risk, that of direct and constant trained supervision in a safe environment, has an enormous negative impact on the lifestyles of patients who require frequent treatment and on labor requirements of the institutions performing such therapies. Thus, there is a perennial need in the art for ultra-safe systems that can be used in a non-clinical setting and/or without the need for highly trained and expensive staff. Currently, there is great interest in ways of providing systems for patients to use at home. One of the risks for such systems is the danger of leaks. As a result, a number of companies have dedicated resources to the solution of the problem of leak detection.

In single-access systems, loss of blood through the patient access and blood circuit can be indirectly detected by detecting the infiltration of air during the draw cycle. Air is typically detected using an ultrasonic air detector on the tubing line, which detects air bubbles in the blood. The detection of air bubbles triggers the system to halt the pump and clamp the line to prevent air bubbles from being injected into the patient. Examples of such systems are described in U.S. Pat. Nos. 3,985,134, 4,614,590, and 5,120,303.

While detection of air infiltration is a reliable technique for detecting leaks in single access systems, the more attractive two-access systems, in which blood is drawn continuously from one access and returned continuously through another, present problems. While a disconnection or leak in the draw line can be sensed by detecting air infiltration, just as with the single needle system, a leak in the return line cannot be so detected. This problem has been addressed in a number of different ways, some of which are generally accepted in the industry.

The first level of protection against return line blood loss is the use of locking luers on all connections, as described in International Standard ISO 594-2 which help to minimize the possibility of spontaneous disconnection during treatment. Care in the connection and taping of lines to the patient's bodies is also a known strategy for minimizing this risk.

A higher level of protection is the provision of venous pressure monitoring, which detects a precipitous decrease in the venous line pressure. This technique is outlined in International Standard IEC 60601-2-16. This approach, although providing some additional protection, is not very robust, because most of the pressure loss in the venous line is in the needle used to access the patient. There is very little pressure change in the venous return line that can be detected in the event of a disconnection, so long as the needle remains attached to the return line. Thus, the pressure signal is very weak. The signal is no stronger for small leaks in the return line, where the pressure changes are too small to be detected with any reliability. One way to compensate for the low pressure signal is to make the system more sensitive, as described in U.S. Pat. No. 6,221,040, but this strategy can cause many false positives. It is inevitable that the sensitivity of the system will have to be traded against the burden of monitoring false alarms. Inevitably this leads to compromises in safety. In addition, pressure sensing methods cannot be used at all for detecting small leaks.

Yet another approach, described for example in PCT application US98/19266, is to place fluid detectors near the patient's access and/or on the floor under the patient. The system responds only after blood has leaked and collected in the vicinity of a fluid detector. A misplaced detector can defeat such a system and the path of a leak cannot be reliably predicted. For instance, a rivulet of blood may adhere to the patient's body and transfer blood to points remote from the detector. Even efforts to avoid this situation can be defeated by movement of the patient, deliberate or inadvertent (e.g., the unconscious movement of a sleeping patient).

Still another device for detecting leaks is described in U.S. Pat. No. 6,044,691. According to the description, the circuit is checked for leaks prior to the treatment operation. For example, a heated fluid may be run through the circuit and its leakage detected by means of a thermistor. The weakness of this approach is immediately apparent: there is no assurance that the system's integrity will persist, throughout the treatment cycle, as confirmed by the pre-treatment test. Thus, this method also fails to address the entire risk.

Yet another device for checking for leaks in return lines is described in U.S. Pat. No. 6,090,048. In the disclosed system, a pressure signal is sensed at the access and used to infer its integrity. The pressure wave may be the patient's pulse or it may be artificially generated by the pump. This approach cannot detect small leaks and is not very sensitive unless powerful pressure waves are used; in which case the effect can produce considerable discomfort in the patient.

Clearly detection of leaks by prior art methods fails to reduce the risk of dangerous blood loss to an acceptable level. In general, the risk of leakage-related deaths increases with the decrease in medical staff per patient driven by the high cost of trained staff. Currently, with lower staffing levels comes the increased risk of unattended leaks. Thus, there has been, and continues to be, a need in the prior art for a foolproof approach to detection of a return line leak or disconnection.

SUMMARY OF THE INVENTION

According to the present invention, leak detection sensitivity and reliability of leak detection are enhanced by combining the detection of fluid leaking from protected blood circuit with detection of air infiltration into the blood circuit. The latter is a new technique described in the commonly assigned pending application "Method and Apparatus for Leak Detection in a Fluid Line," the entirety of which is hereby incorporated by reference as if fully set forth herein in its entirety. The new method identifies leaks in a normally positive pressure part of a circuit where infiltration does not ordinarily result from a leak. The portion that is ordinarily under negative pressure experiences infiltration which may be detected by an air sensor in a blood processing machine. A fluid detector is located within the blood processing machine and detects any leakage from within the housing of the blood processing machine. The lines extending outside the blood processing machine are protected by the detection of leaks by detecting air infiltration in accord with the method and apparatus described in the application incorporated by reference above.

In an embodiment of the invention, a funnel is incorporated in the blood processing machine to guide and concentrate any blood leaking from the circuit into a fluid detector. The fluid detector may be a continuity sensor relying on electrolyte conduction to sense fluid, a temperature sensor, a pH sensor, an impact sensor detecting drops, or any other sensor effective to detect blood leaking out of the circuit.

Another embodiment allows retrofit to an existing blood processing machine. This embodiment may include a funnel added to the bottom to collect any blood leaking from it. The funnel may be a flexible bag-like component that can be attached with hook and loop-type connectors to the bottom of the blood processing machine. If a retrofit embodiment of the leak detection device of the application incorporated by reference above is used with a conventional blood processing machine, the retrofit funnel may be made large enough to cover both the blood processing machine, the retrofit leak detector device, and the connecting tubing.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE EMBODIMENTS

Figure 1:
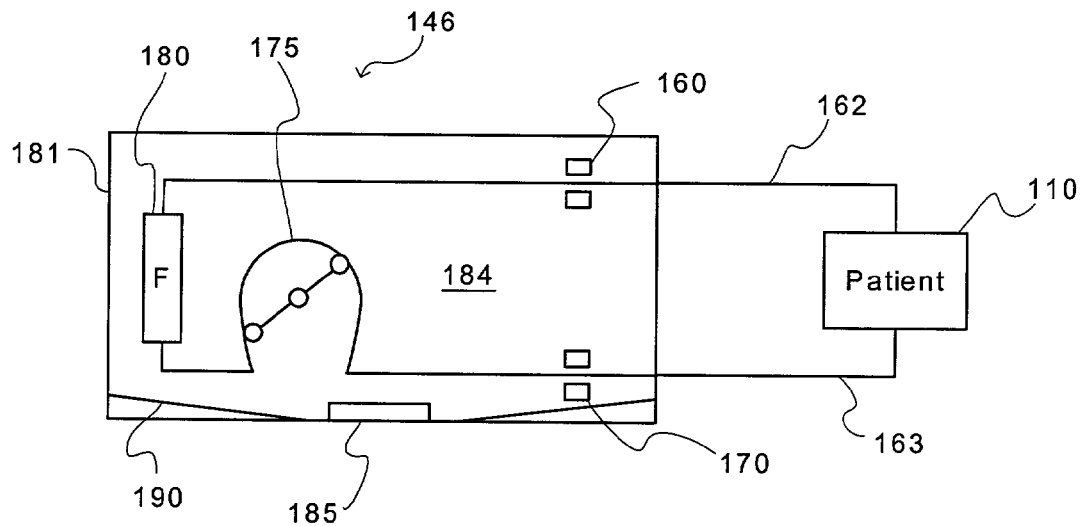
FIG. 1 is an illustration of a blood processing machine with leak detection built into it including a fluid sensor to detect blood outside the blood circuit and one or more air sensors for detecting the infiltration of air into the blood circuit due to a leak.

Referring now to FIG. 1, a blood processing machine 146 for treating a patient 110 has leak detection components built into it. The machine includes air sensors 160 and 170, a filter 180, and a reversible pump 175, the latter being one mechanism for reversing flow to test the return circuit as discussed in the patent application incorporated by reference above.

During operation, the pump 175 reverses periodically to test the normally high-pressure side 162 of the circuit. When the pump 175 reverses, a negative pressure is generated on the normally high-pressure side 162 of the circuit that will draw air into any leaks. The air will then be detected by air sensor 160. During forward operation, the air sensor 170 detects any leaks because air will infiltrate the normally low-pressure side 163 of the circuit. Thus, the two air sensors 160 and 170 quickly detect any leaks in when the pump is driven in forward and reverse directions, respectively.

Within a housing 181, a funnel 190 directs any blood leaking from the housed portion 184 of the circuit toward a fluid detector 185. Any leaks occurring in the housed portion 184 will be directed by the funnel 190 toward the fluid detector 185. The fluid detector 185 may be any suitable device for detecting blood, for example, a continuity tester responsive to electrolytic conduction, a temperature sensor, a pH sensor, an impact sensor detecting drops, or any other sensor effective to detect blood leaking out of the circuit 184.

The fluid detector 185 may be linked to the same alarm system as the air sensors 160 and 170. The system may be programmed such that the air sensors 160 and 170 "protect" the access lines 162 and 163 outside the machine by providing for flow reversal only as far as necessary to detect leaks in normally-positively pressurized lines. In that case, the fluid detector 185 may provide warning for any leaks inside the blood processing machine 146 and the air sensors 160 and 170 protection for the access lines.

Alternatively, the system may be programmed such that the protection fields overlap, that is, the pump 175 reverses for a sufficient displacement of blood that any leaks at all may be detected while air detection provides another level of protection. In this case, if the sensitivity of the air detector 160 and 170-based leak detection is raised, but modulated according to the status of the fluid detector 165 signal such that an air sensor signal of a low level indicating a leak does not result in an alarm condition unless it is accompanied by a leak indication by the fluid detector 165, false positives arising from the air sensors can be reduced and the sensitivity of the system enhanced. The sensitivity of the fluid detector may be similarly increased, resulting in the possibility of detecting smaller leaks than a system calibrated to operate without such "cooperation" among leak detection subsystems. Note that the overlap in protection zones can be increased by providing one or more additional fluid detectors under the lines or an extension to the funnel 190 to catch fluid leaking from the access lines 162 and 163.

Note that the configuration of FIG. 1 need not have two air sensors as should be clear from the application incorporated by reference. A single air sensor can serve as a detector of infiltration in both lines.

Figure 2:
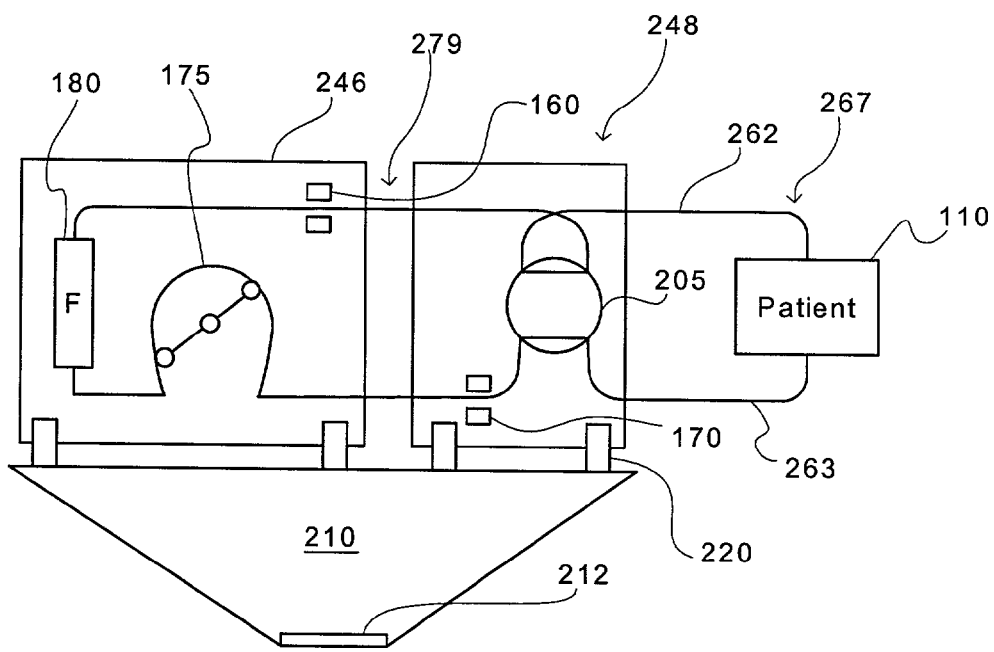
FIG. 2 is an illustration of a retrofit configuration that provides the functionality of the device of FIG. 1 for a conventional blood processing machine without leak detection, the illustration showing connected to the conventional blood processing machine, a retrofit device providing air-detection and a retrofit funnel and fluid sensor to detect blood outside the blood circuit.
Figure 3:
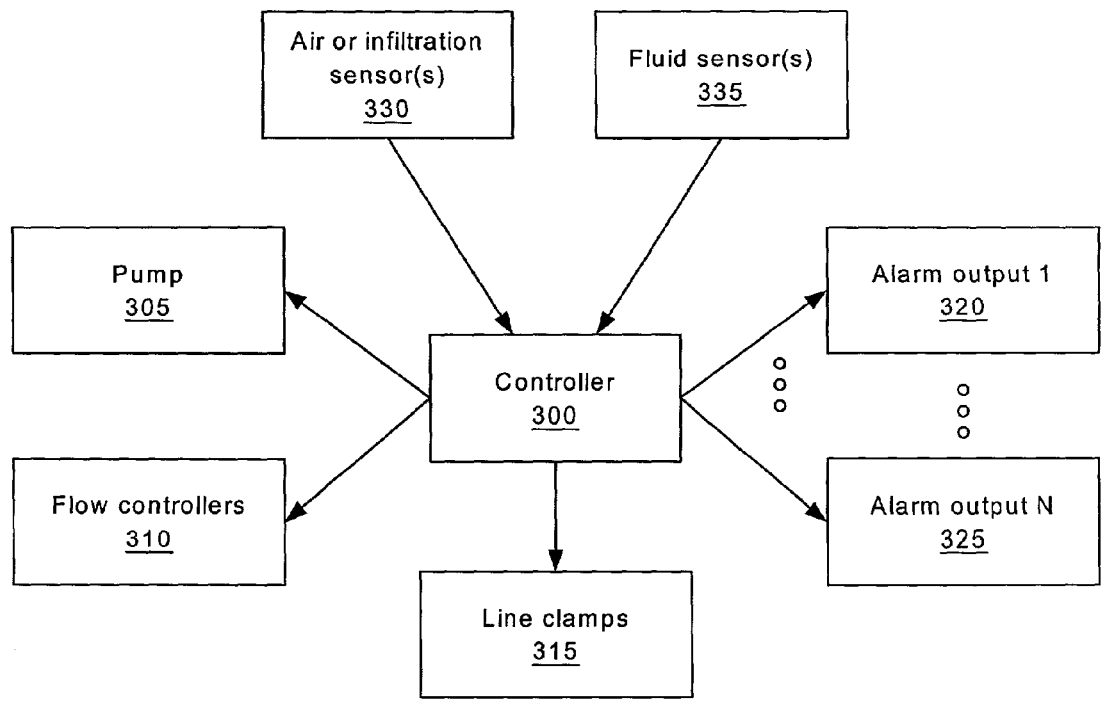
FIG. 3 is a block diagram of a control system consistent with various embodiments of the invention.

Referring now to FIG. 3, air or infiltration sensors 330 and one or more fluid sensors 335 are connected to send signals to a controller 300. The controller 300, in turn, controls alarms 1-N 320 . . . 325, the pump 305, a flow controller such as four-way valve (See FIG. 2 and attending discussion) and line clamps 315. To stop any loss of blood, the lines of the blood circuit may be clamped by one or more line clamps 315 and the pump 305 shut down. The controller 300 may be a programmable processor, a simple relay network, or any other suitable type of control device.

The logic of the control algorithm may be a simple invocation of a shut-down and alarm procedure when a signal from either the air or infiltration sensor(s) 330 or the fluid sensor(s) 335 goes beyond a threshold. The shut-down and alarm procedure may be one known in the prior art or any other suitable process up to the discretion of the system designer.

Referring now to FIG. 2, in an alternative design that is suitable for retrofit to a conventional blood processing machine 246. A separate leak detection device 248 periodically reverses flow through the patient side of the blood circuit 267 so that a negative pressure is generated in a normally positive pressure side 262 of the blood circuit. The leak detection device does this by switching a four-way valve 205 as taught in the application incorporated by reference above. The air sensors 160 and 170 serve the same purpose as in the embodiment of FIG. 1. That is, air will infiltrate either line, normal-return 262 or normal draw 263, at some point when the flow is in a corresponding direction. The air infiltration, and thereby the leak, will ultimately be detected by one of the air sensors 160 and 170.

Any blood leaking from any part of the blood processing machine 246, the leak detecting device 248, or the connecting portions of the circuit 279 are collected by a retrofit funnel attachment 210 and directed to a fluid sensor 212 therein. The retrofit funnel 210 may be a simple flexible bag-like structure or a rigid structure. The latter may permit a one-size-fits-all product that can be adapted to any size blood processing machine 246 and leak detection device 248. The funnel 210 may be attached using any suitable fasteners 220 such as hook and loop or bolt-on fasteners.

Figure 4:
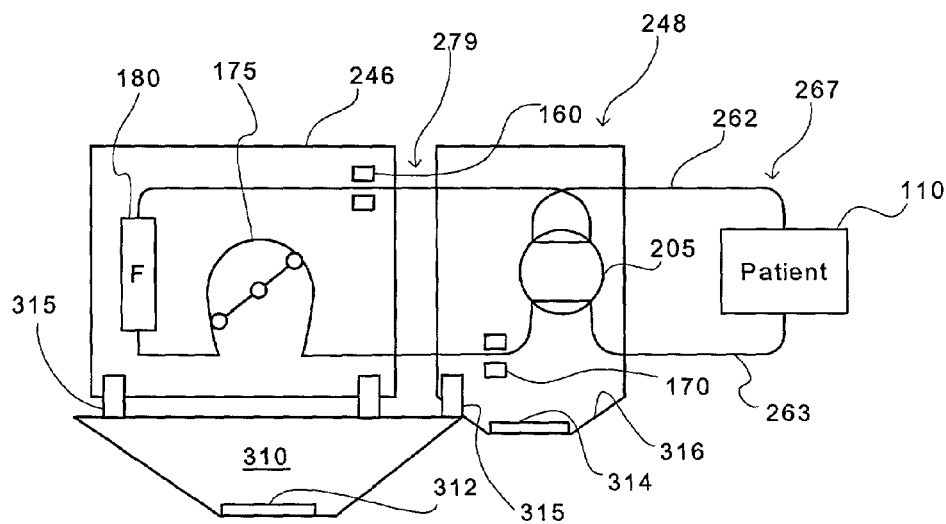
FIG. 4 is a figurative diagram of a retrofit configuration having a conventional blood processing machine and a leak detection portion combining both fluid detection and air infiltration detection to provide full coverage of a blood circuit.

Referring to FIG. 4, the leak detection device may have a housing funnel 316 with a fluid detector 314 built into it. In this case, a retrofit funnel 310 and fluid detector 312 need only be attached to the blood processing machine and adapted to catch any leaks from the connecting lines 279 as illustrated. The funnel 310 may be attached by any suitable means such as by hook and loop fasteners 315. Again the funnel 310 may be made of flexible plastic to permit it to be fit around obstacles or differently-size machines.

Figure 5:
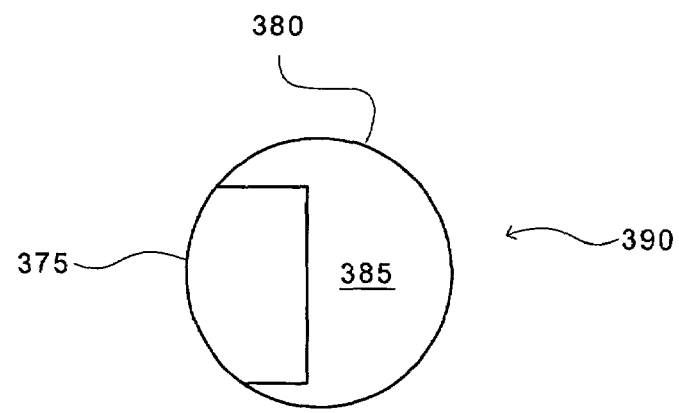
FIG. 5 is an illustration of a fluid-detecting transponder according to another embodiment of the invention.
Figure 6:
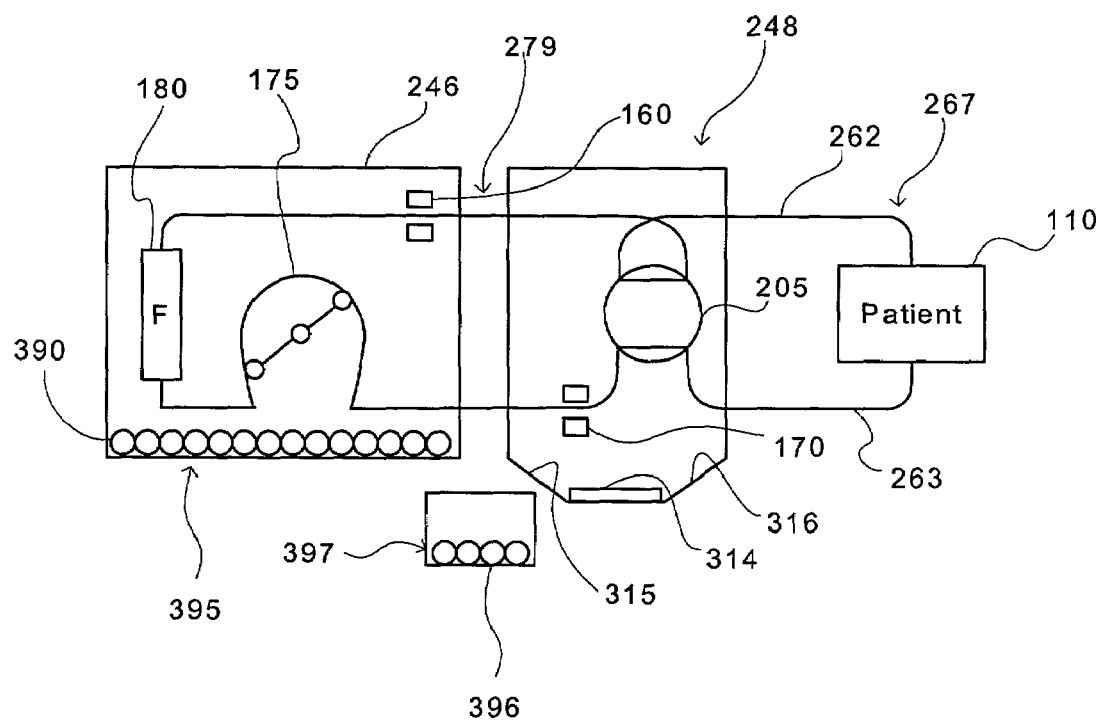
FIG. 6 is an illustration of a leak detection embodiment making use of the transponder of FIG. 5.

Referring now to FIG. 5, a fluid detecting transponder 390 detects fluid and emits a wireless signal in response to the detection. The transponder has a fluid sensor portion 385 and a transmitter portion 375. The transponder has a power source (not shown) such as a battery. The transmitter portion 375 may emit a radio or acoustic signal. Referring now also to FIG. 6, one or more transponders 390 may be placed inside the housing of a blood processing machine 246 as illustrated at 395. Alternatively, in systems where the blood circuit is mounted to a panel and exposed, the transponders 390 may be placed below the blood processing machine in a trough or other open container 396 as illustrated at 397.

Figure 7:
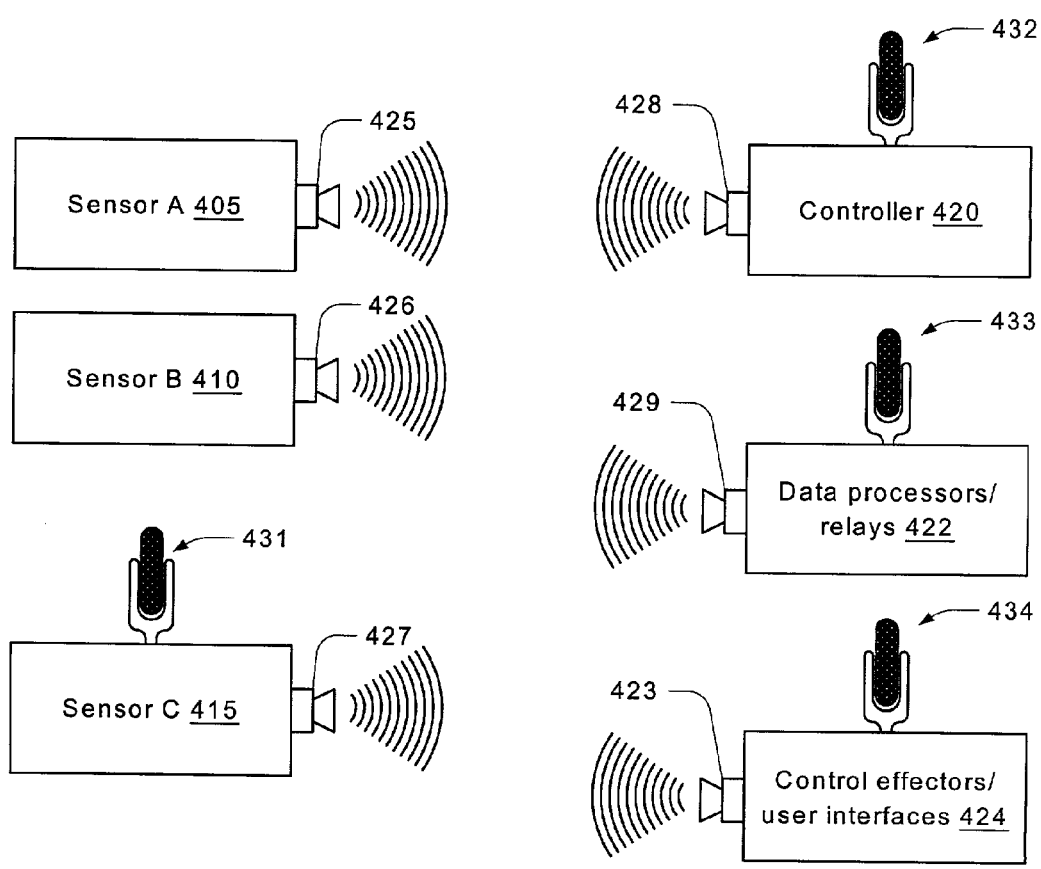
FIG. 7 is an illustration of an acoustic network for connecting components of various embodiments of the current invention.

Referring now to FIG. 7, a multiple-input/multiple-level leak detection system may employ multiple sensors, such as in the embodiment of FIG. 6. The many sensors are indicated at 405, 410, . . . 415 to communicate with a controller 420 and for the controller 420 to communicate with multiple output devices and user interfaces 424 and data processors and relays 422. In the present embodiment, rather than wire the components together, they communicate with each other using respective sound signal generators 425, 426, 427, 428, 429, and 423 and receivers 431, 432, 433, and 434, for example, as in the transducer 390 of FIG. 5.

The signals are preferably articulated sufficiently to encode unique identifiers so that multiple systems within "hearing" range of one another do not cause interference. Also, the sound pattern may encode information other than an identifier of the transmitter and/or receiver, for example, it can encode a type of status or magnitude of a detected condition, such as heart rate or degree of wetting of a fluid detector. The sounds may be above or below the frequency range of human hearing to avoid the subjective impact. Alternatively, the signals may be spread over ranges of frequency by modulating with a pseudorandom code. The subject effect of such spread-spectrum signals can be very low due to the noise-like nature of the sound and the low power levels required for data transmission.

In a system where the components of a multiple input alarm system may only need to communicate with each other when conditions reach an abnormal status, the audibility of a given signal may pose a problem. The particular alarm system application, therefore, may provide an inoffensive context for using acoustic signals to communicate between components; a sort of "chirp network" to interconnect the functional components of the system. In fact, the audibility of communication signals may provide a benefit. For example, an attendant called to a location by a remote-station alarm may be greeted not only by a user interface indicating the nature of the problem but also by the sending unit's characteristic audio signal. This may reinforce the output from the user interface increasing comprehension by the attendant of the alarm condition that occurred.

Some sensors, such as indicated for sensor C 415, may have the ability to receive as well as send signals. The data processor/relay 422 may be, for example, a component of the acoustic network that processes information outside the controller 420. For example, it could reduce data from other sources unburdening the controller 420 or permitting feature-upgrades to the controller without requiring its replacement or modification.

Although the invention has been described in connection with a blood circuit having simply a pump and a filter, such as a dialysis or hemofiltration system, this type of circuit was only used as an example for purposes of discussion. It should be clear from the disclosure that the invention is applicable to any kind of blood processing system, including hemodiafiltration, blood and blood component collection, plasmaphresis, aphresis, blood oxygenation, blood factor (e.g., stem cell) harvesting and all manner of extracorporeal blood processing. The invention is also applicable to infusion systems as should be clear from the current specification, particularly in combination with the teachings of the application incorporated by reference above.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for detecting leaks in a blood circuit, comprising:
    a first leak detector that detects leaks by sensing any presence of blood outside said blood circuit, said first leak detector being located to detect leaks from a first portion of said blood circuit located remote from a patient;
    said outside being a non-wetted environment of said blood circuit;
    a second leak detector that detects leaks by sensing air infiltration into lines under negative pressure;
    said second leak detector being configured to detect leaks in lines connecting said patient to said first portion;
    a mechanism that insures that at least part of said lines are under negative pressure at least part of the time during a treatment such that a detectable air infiltration indicates a presence of a leak in said lines;
    an alarm device that outputs an alarm signal responsively to a detection of a leak by said first or second leak detector.

2. A device as in claim 1, wherein said second leak detector includes a liquid fluid sensor below said circuit first portion.

3. A device as in claim 1, where in said first leak detector is located below said first portion, said device further comprising a flow director to concentrate any leaking fluid toward said first leak detector.

4. A device for detecting a leak from a blood circuit of an extracoxporeal blood treatment machine, comprising:
    respective detectors located to detect leaks of blood from respective portions of a blood circuit;
    at least two of said respective detectors including sensors configured to detect different physical effects correlated with one or more blood leaks;
    said respective portions including parts that are non-overlapping;
    wherein said different physical effects include the infiltration of air into a blood circuit and the presence of blood outside said blood circuit;
    said outside being a non-wetted environment of said blood circuit;
    an output device connected to receive signals from said respective detectors and to output a signal responsively thereto and an alarm connected to generate an output responsively to said signal;
    wherein said output device and detectors are configured such that said signal indicates a leak if either of said respective different physical effects indicates a leak;
    wherein at least one of said detectors includes an air sensor or bubble sensor and a mechanism adapted to periodically generate a negative pressure in said blood circuit such that air infiltrates said blood circuit through any openings therein.

5. A device as in claim 4, wherein said mechanism includes a mechanism adapted to reverse flow.

6. A device for detecting leaks in an extracorporeal blood circuit, comprising:
    a liquid detector positioned to detect blood or liquid outside a first portion of a blood circuit;
    said outside being a non-wetted environment of said blood circuit;
    an air detector positioned to detect air inside a second portion of the blood circuit that is remote from the first portion;
    a positive displacement mechanism configured to periodically generate a negative pressure in said blood circuit such that air is caused to be infiltrated in portions that are otherwise not under negative pressure; and
    an alarm configured to signify the occurrence of a leak in response to either or both of said liquid detector and said air detector.

7. A device as in claim 6, wherein said positive displacement mechanism includes a reversible pump in said blood circuit.

8. A device as in claim 6, wherein said liquid detector is positioned within a housing that houses said blood circuit first portion.

9. A device as in claim 8, wherein said housing includes a funnel shaped portion to guide leaking blood to said liquid detector.

10. A method for detecting leaks in a blood treatment machine, comprising the steps of:
    during a treatment operation, detecting liquid outside a blood circuit, at least a first portion of which is under non-negative pressure during a treatment operation;
    said outside being a non-wetted environment of said blood circuit;
    creating a temporary negative pressure at least two times during said treatment operation in at least a second portion of said blood circuit effective to cause air to infiltrate said second portion;
    detecting said air caused to infiltrate by said step of creating; at least one of halting a pumping of blood in either or both of said first and second blood circuit portions or generating an alarm signal responsively to a result of either or both of said steps of detecting.

11. A device for detecting leaks in a blood treatment circuit, comprising:
- a first leak detector that detects leaks by sensing liquid in an otherwise dry outside environment of said blood treatment circuit, said first leak detector being located to detect leaks from at least a first portion of said blood treatment circuit;
- a second leak detector tat detects leaks by sensing air or bubble infiltration into lines of said blood treatment circuit under negative pressure;
- said second leak detector being configured to detect leaks at least in said lines of said blood treatment circuit that connect said patient to said first portion;
- a positive displacement mechanism that insures that at least part of said lines are under negative pressure at least part of the time during a treatment such that a detectable air or bubble infiltration indicates a presence of a leak in said lines;
- an alarm device that monitors said first and second leak detectors during a treatment and generates a response signal responsively to a detection of a leak by said first or second leak detector.

12. A device as in claim 11, wherein said alarm device includes an audio alarm signal generator.

13. A device as in claim 11, wherein said positive displacement mechanism includes a pump with a reversible flow direction.

* * * * *